United States Patent [19]

Walker et al.

[11] Patent Number: 5,270,184

[45] Date of Patent: Dec. 14, 1993

[54] NUCLEIC ACID TARGET GENERATION

[75] Inventors: George T. Walker, Chapel Hill; Michael C. Little, Raleigh; James G. Nadeau, Durham, all of N.C.

[73] Assignee: Becton, Dickinson and Company, Franklin Lakes, N.J.

[21] Appl. No.: 794,399

[22] Filed: Nov. 19, 1991

[51] Int. Cl.$^5$ .............................................. C12P 19/34
[52] U.S. Cl. ................................. 435/91.2; 435/91.21
[58] Field of Search ................... 435/6.91; 536/27; 436/501, 94

[56] References Cited

U.S. PATENT DOCUMENTS 4,683,195  7/1987  Mullis et al. ......................... 435/6
5,106,727  4/1992  Hartley ................................ 435/6

FOREIGN PATENT DOCUMENTS 0200362  12/1986  European Pat. Off. .
0395398  10/1990  European Pat. Off. .
0497272   8/1992  European Pat. Off. .

WO90/14439 11/1990 PCT Int'l Appl. .................... 435/6

OTHER PUBLICATIONS

Maniatis et al., *Molecular Cloning a Lab Manual,* Cold Spring Harbor Lab., 1992, pp. 109, 114.
John C. Guatelli et al., *Proc. Natl. Acad. Sci. USA* (1990)
Deborah Y. Kwoh et al., *ABL* (Oct. 1990) p. 14.

*Primary Examiner*—Stephanie W. Zitomer
*Attorney, Agent, or Firm*—Donna R. Fugit

[57] ABSTRACT

The invention is a method for generating nucleic acid sequences ends which comprises;
  (a) hybridizing a primer to a nucleic acid sequence,
  (b) hybridizing a primer to the nucleic acid sequence in (a) located 5' to the primer in (a), and
  (c) polymerizing both primers so that the primer in (a) is displaced from the nucleic acid sequence.

The invention provides a method for generating target nucleic acid sequences for subsequent amplification. The method is applicable to both DNA and RNA.

7 Claims, 4 Drawing Sheets

HYBRIDIZE SDA PRIMERS TO DISPLACED STRANDS

NUCLEIC ACID TARGET GENERATION

FIELD OF THE INVENTION

This invention relates to a method for preparing a target nucleic acid prior to amplification.

BACKGROUND OF THE INVENTION

Nucleic acids may be either in the form of deoxyribonucleic acids (DNA) or in the form of ribonucleic acids (RNA). DNA and RNA are high molecular weight polymers formed from many nucleotide building blocks. Each nucleotide is composed of a base (a purine or a pyrimidine), a sugar (either ribose or deoxyribose) and a molecule of phosphoric acid. DNA is composed of the sugar deoxyribose and the bases adenine (A), guanine (G), cytosine (C) and thymine (T).

The nucleotides are assembled into a linear chain to form the genetic code. Each sequence of three nucleotides can be "read" as the code for one amino acid through the process of translation (DNA must first be converted into RNA through the process of transcription). By varying the combination of bases in each three base sequence, different amino acids are coded for. By linking various three base sequences together, a sequence of amino acids can be made which forms proteins and polypeptides. The entire coding unit for one protein is referred to as a gene. There can be one or more copies of a gene in an organism. Some genes are present in hundreds or thousands of copies, others are present only as a single copy.

Regardless of the number of copies, genes are linked together in an organism to form higher structural units referred to as chromosomes in higher organisms. In some lower organisms, genes may occur in extra chromosomal units referred to as plasmids. Genes need not be linked directly to each other in an end-to-end fashion. Certain non coding regions (i.e., introns: sequences of bases that do not translate into amino acids) may occur between genes or within a gene. The arrangement of nucleotides in an organism determines its genetic makeup which may be referred to as its genome (hence, DNA isolated from an organism is referred to as genomic DNA).

DNA in most organisms is arranged in the form of a duplex wherein two strands of DNA are paired together in the familiar double helix. In this model, hydrogen bonds are formed between A and T and between C and G on the paired strands. Thus, on one strand, the sequence ATCG (5'→3') will have on its complementary strand the sequence TAGC (3'→5'). Both strands, however, contain the same genetic code only in a complementary base-paired manner. One could read, therefore, either strand of DNA in order to determine the genetic sequence coded for.

For a further description of the organization, structure and function of nucleic acids, see Watson, *Molecular Biology of the Gene*, W. J. Benjamin, Inc. (3rd edit. 1976), especially Chapters 6-14.

Understanding and determining the genetic sequence of nucleic acids present in a sample is important for many reasons. First, a number of diseases are genetic in the sense that the nucleotide sequence for a "normal" gene is in some manner changed. Such a change could arise by the substitution of one base for another. Given that three bases code for a single amino acid, a change in one base (referred to as a point mutation) could result in a change in the amino acid which, in turn, could result in a defective protein being made in a cell. Sickle cell anemia is a classic example of such a genetic defect caused by a change in a single base in a single gene. Other examples of diseases caused by single gene defects include Factor IX and Factor VIII deficiency, adenosine deaminase deficiency, purine nucleotide phosphorylase deficiency, ornithine transcarbamylase deficiency, argininsuccinate synthetase deficiency, beta-thalassemia, $\alpha_1$ antitrypsin deficiency, glucocerebrosidase deficiency, phenylalanine hydroxylase deficiency and hypoxanthine-guanine phosphoribosyltransferase deficiency. Still other diseases, such as cancers, are believed to be caused by the activation, increase in copy number and/or removal of suppression of genes known to be present in the genome (referred to as oncogenes). Examples of oncogenes believed to be relevant to certain cancers include N myc for neuroblastomas, retinoblastomas and small cell lung cancers and c-abl for chronic myelogenous leukemia. For a further description of the relevance of oncogenes to the diagnosis of cancers and for a listing of specific oncogenes, see Weinberg, Sci. Amer., Nov. 1983, Slamon et al., Science, 224:256 (1984), U.S Pat. No. 4,699,877 and 4,918,162.

Second, in addition to changes in the sequence of nucleic acids, there are genetic changes that occur on a structural level. Such changes include insertions, deletions and translocations along a chromosome and include increased or decreased numbers of chromosomes. In the former instance, such changes can result from events referred to as crossing over where strands of DNA from one chromosome exchange various lengths of DNA with another chromosome. Thus, for example, in a "normal" individual, the gene for protein "X" might reside on chromosome 1; after a crossing over event, that gene could now have been translocated to chromosome 4 (with or without an equal exchange of DNA from chromosome 4 to chromosome 1) and the individual may not produce X.

In the instance of increased or decreased chromosome number (referred to as aneuploidy), instead of a "normal" individual having the correct number of copies of each chromosome (e.g., two of each in humans [other than the X and Y chromosomes]), a different number occurs. In humans, for example, Down's syndrome is the result of having three copies of chromosome 21 instead of the normal two copies. Other aneuploid conditions result from trisomies involving chromosomes 13 and 18.

Third, infectious diseases can be caused by parasites, microorganisms and viruses all of which have their own nucleic acids. The presence of these organisms in a sample of biological material often is determined by a number of traditional methods (e.g., culture). Because each organism has its own genome, however, if there are genes or sequences of nucleic acids that are specific to a single species (to several related species, to a genus or to a higher level of relationship), the genome will provide a "fingerprint" for that organism (or species, etc.). Examples of viruses to which this invention is applicable include HIV, HPV, EBV, HSV, Hepatitis B and C and CMV. Examples of microorganisms to which this invention is applicable include bacteria and more particularly include *H. influenzae*, mycoplasma, legionella, mycobacteria, chlamydia, candida, gonocci, shigella and salmonella.

In each example set forth above, by identifying one or more sequences that are specific for a diseases or organism, one can isolate nucleic acids from a sample and determine if that sequence is present. A number of methods have been developed in an attempt to do this.

While it is critical that one or more sequences specific for a disease or organism be identified, it is not important to the practice of this invention what the target sequences are or how they are identified. The most straightforward means to detect the presence of a target sequence in a sample of nucleic acids is to synthesize a probe sequence complementary to the target nucleic acid (instrumentation, such as the Applied BioSystems 380B, is presently used to synthesize nucleic acid sequences for this purpose). The synthesized probe sequence then can be applied to a sample containing nucleic acids and, if the target sequence is present, the probe will bind to it to form a reaction product. In the absence of a target sequence and barring non specific binding, no reaction product will be formed. If the synthesized probe is tagged with a detectable label, the reaction product can be detected by measuring the amount of label present Southern blotting is one example where this method is used.

A difficulty with this approach, however, is that it is not readily applicable to those instances where the number of copies of the target sequence present in a sample is low (i.e., less than $10^7$). In such instances, it is difficult to distinguish signal from noise (i.e., true binding between probe and target sequences from non specific binding between probe and non target sequences). One way around this problem is to increase the signal Accordingly, a number of methods have been described to amplify the target sequences present in a sample.

One of the best known amplification methods is the polymerase chain reaction (referred to as PCR) which is described in detail in U.S. Pat. Nos. 4,683,195, 4,683,202 and 4,800,159. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated.

Another method for amplification is described in EPA No. 320,308, published Jun. 14, 1989, which is the ligase chain reaction (referred to as LCR). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence but does not describe an amplification step.

A still further amplification method is described in PCT Appl. No. PCT/US87/00880, published Oct. 22, 1987, and is referred to as the Qbeta Replicase method.

In this method, a replicative sequence of RNA which has a region complementary to that of a target is added to a sample in the presence of an RNA polymerase. The polymerase will copy the replicative sequence which can then be detected.

Still other amplification methods are described in GB Appl. No. 2 202 328, published Sep. 21, 1988, and in PCT Appl. No. PCT/US89/01025, published Oct. 5, 1989. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence. And finally U.S. patent application Ser. No. 07/648,257 filed Jan. 31, 1991 discloses and claims a method for amplifying nucleic acid (referred to as strand displacement amplification) which comprises target generation prior to amplification in which restriction enzymes are employed.

Each of the above referenced amplification methods benefit from access to the desired nucleic acid sequence to be amplified. In addition, the need to generate amplifiable target fragments with defined 5'- and 3'-ends (i.e., ending at specific nucleotide positions) is a continually sought after goal.

SUMMARY OF THE INVENTION

The invention is a method for generating nucleic acid sequences which comprises;
 (a) hybridizing a primer to a nucleic acid sequence,
 (b) hybridizing a primer to the nucleic acid sequence in (a) located 5' to the primer in (a), and
 (c) polymerizing both primers so that the primer in (a) is displaced from the nucleic acid sequence.

The invention provides a method for generating target nucleic acid sequences with defined 5'- and 3'-ends for subsequent amplification and cloning. The method is applicable to both DNA and RNA.

In addition, the method can employ a heat step after (c), above, and repeat over and over.

When the target fragments comprise double stranded nucleic acids, the method further comprises denaturing the nucleic acid fragments to form single stranded target sequences only once. Where the nucleic acids comprise RNA, it is preferable to use reverse transcriptase to convert RNA to DNA.

Subsequent strand displacement amplification (SDA) is enhanced because a larger number of modified nicking sites are generated from each original target strand. The previously described SDA method involved target restriction prior to binding primers and produced only two double stranded fragments with a modified nicking site at just one end. The restriction step was necessary to provide target fragments with defined 5'-and 3'-ends. Subsequent binding of the SDA primers to the 3'-ends of these target fragments and subsequent extension by an exonuclease deficient form of klenow (exo⁻klenow) provided nicking enzyme recognition sites from which SDA initiated. The current target generation method produces four double stranded fragments with a total of six modified nicking sites (see FIG. 1). In addition, target sequences can now be chosen without regard for convenient flanking restriction sites. Finally, SDA can now be applied to either double or single stranded target DNA target samples. Previously, targets had to be double stranded for cleavage by the restriction enzyme(s). As used in this document, "nicking" refers to preferential cleavage of one of two strands present in a double-stranded recognition site.

The invention further relates to methods for the separation and/or detection of amplified products generated by the invention. Methods for separation of amplified products comprise magnetic separation, membrane capture and capture on solid supports. In each method, a capture moiety may be bound to a magnetic bead, membrane or solid support. The beads, membrane or solid support then can be assayed for the presence or absence of amplified products. An example of a capture moiety includes a nucleic sequence complementary to the amplified products produced and an antibody directed against a receptor incorporated into the primer or amplified product. The separation system may or may not be coupled to a detection system.

The invention further relates to methods of generating amplified products which can function as probes or templates for sequence analysis. In this format, the above described method and steps are used to generate amplified products. The amplified products can then be treated to remove the nicking enzyme recognition sequence from the amplified product, for example by using a restriction enzyme. In this manner, the recognition sequence is removed and the remaining amplified product comprises a probe which can he used in other systems.

BRIEF DESCRIPTION OF THE FIGURES

FIG. 1 Target generation scheme for strand displacement amplification. This figure depicts the initial steps which transform the original target sequence into "steady state" amplification as depicted in FIG. 2. A target DNA sample is heat denatured. Four primers ($B_1$, $B_2$, $S_1$ and $S_2$), present in excess, bind the target strands at positions flanking the sequence to be amplified. Primers $S_1$ and $S_2$ have HincII recognition sequences at their 5'-ends. The four primers are simultaneously extended by exo⁻ klenow using dGTP, dCTP, TTP and dATP(aS). Extension of $B_1$ displaces the extension product from primer $S_1$ ($S_1$-ext). Likewise, extension of $B_2$ displaces the $S_2$ extension product, $S_2$-ext. $B_2$ and $S_2$ bind to displaced $S_1$-ext. $B_1$ and $S_1$ bind to displaced $S_2$-ext. Extension and displacement reactions on templates $S_1$-ext and $S_2$-ext produce two fragments with a hemiphosphorothioate HincII site at each end and two longer fragments with a hemiohosphorothioate HincII site at just one end. HincII nicking and exo⁻ klenow extension/displacement reactions initiate at these four fragments, quickly reaching the "steady state" set of reactions depicted in FIG. 2. Sense and antisense DNA strands are differentiated by thin and thick lines. HincII recognition sequences are depicted by raised portions on the lines.

FIG. 2 The "steady-state" series of strand displacement amplification (SDA) reactions. The following reaction steps continuously cycle during the course of amplification. Present in excess are two SDA primers ($S_1$ and $S_2$). The 3'-end of $S_1$ binds to the 3'-end of a displaced strand serving as target ($T_1$), forming a duplex with 5'-overhangs. Likewise, $S_2$ binds to the displaced strand, $T_2$. The 5'-overhangs of $S_1$ and $S_2$ contain a recognition sequence (5'GTTGAC3') for the restriction enzyme HincII. Exo⁻ klenow extends the 3'-ends of the duplexes using dGTP, cCTP, TTP and dATP(αS), which produces hemiphosphorothioate recognition sites on $S_1T_1$ and $S_2T_2$. HincII nicks the unprotected primer strands of the hemiphosphorothioate recognition sites, leaving intact the modified complementary strands. Exo⁻ klenow extends the 3'-end at the nick on $S_1T_1$ and displaces the downstream strand that is functionally equivalent to $T_2$. Likewise, extension at the nick on $S_2T_2$ results in displacement of a downstream strand functionally equivalent to $T_1$. Nicking and polymerization/displacement steps cycle continuously on $S_1T_1$ and $S_2T_2$ because extension at a nick regenerates a nickable HincII site. Target amplification is exponential because strands displaced from $S_1T_1$ serve as target for $S_2$ while strands displaced from $S_2T_2$ serve as target for $S_1$. Sense and antisense DNA strands are differentiated by thin and thick lines. HincII recognition sequences are depicted by raised portions on the lines. The partial HincII recognition sequences 5'GAC and its complement 5'GTC are present at the 5'- and 3'-ends of displaced strands, respectively, as represented by small boxes.

DETAILED DESCRIPTION

To practice this invention, a sample may be isolated from any material suspected of containing the target nucleic acid sequence. For animals, preferably, mammals, and more preferably humans, the sources of such materials may comprise blood, bone marrow, lymph, hard tissues (e.g., liver, spleen, kidney, lung, ovary, etc.), sputum, feces and urine. Other sources of material may be derived from plants, soil and other materials suspected of containing biological organisms.

The isolation of nucleic acids from these materials can be done any number of ways. Such methods include the use of detergent lysates, sonication, vortexing with glass beads and a French press. In some instances, it may be advantageous to purify the nucleic acids isolated (e.g., where endogenous nucleases are present). In those instances, purification of the nucleic acids may be accomplished by phenol extraction, chromatography, ion exchange, gel electrophoresis or density dependent centrifugation.

Once the nucleic acids are isolated, it will be assumed for purposes of illustration herein only that the genomic nucleic acid is DNA and is double stranded.

Figure 1:
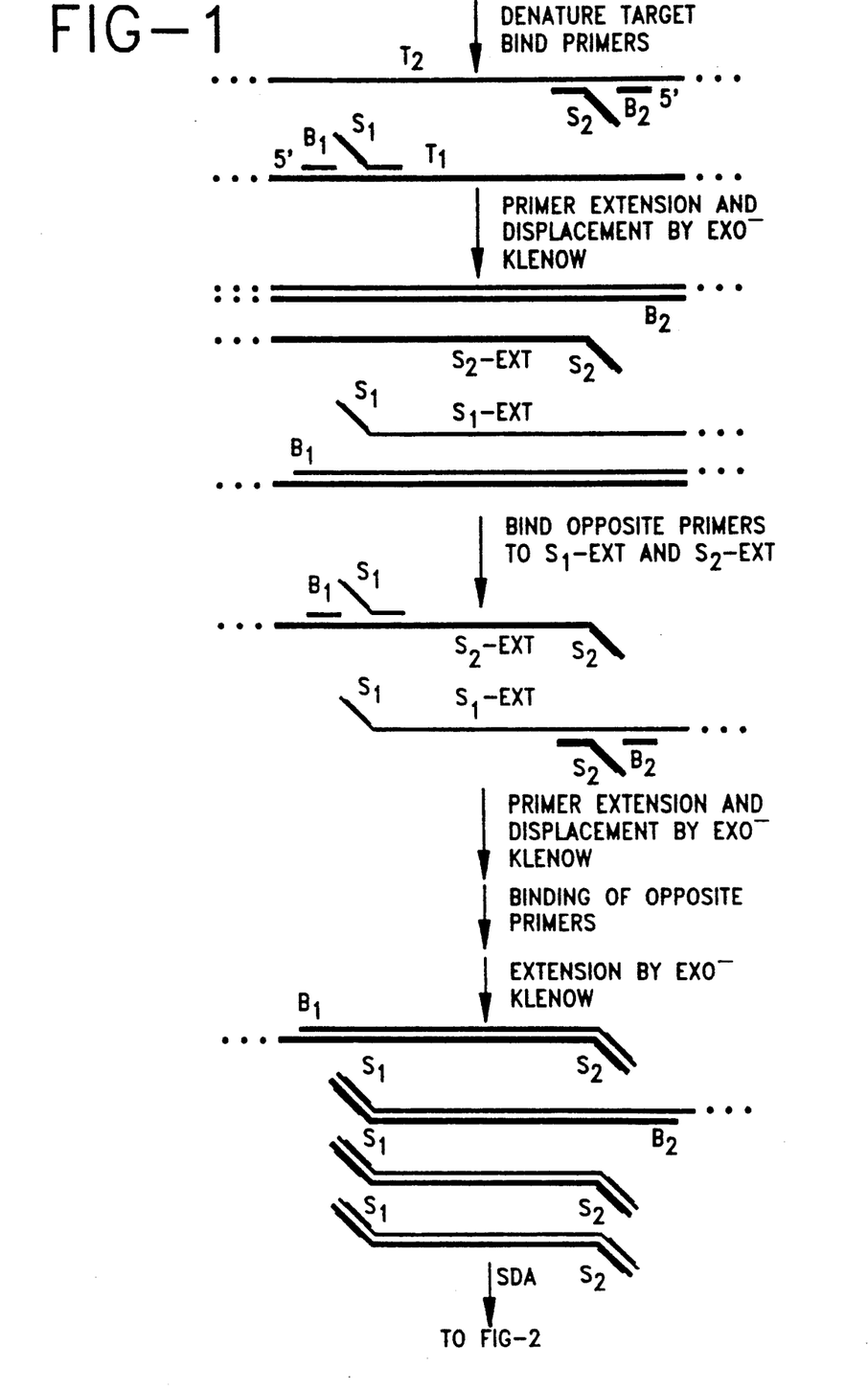

To begin target generation according to this invention for subsequent SDA, the nucleic acid to be amplified (e.g., target) is heat denatured in the presence of an excess of 4 primers (FIG. 1). Two primers ($S_1$ and $S_2$) are typical SDA primers, with target binding regions at their 3'-ends and nicking enzyme recognition sequences located 5'- to the target complementary sequences. (Two SDA primers ($S_1$ and $S_2$) are necessary for exponential amplification, only one SDA primer ($S_1$ or $S_2$) is necessary for linear amplification. The other two primers ($B_1$ and $B_2$) consist simply of target binding regions. (Only one upstream primer, $B_1$ or $B_2$, is absolutely necessary). $S_1$ and $S_2$ bind to opposite strands of the target at positions flanking the sequence to be amplified. $B_1$ and $B_2$ bind upstream of $S_1$ and $S_2$, respectively. Exo$^-$ klenow simultaneously extends all 4 primers using 3 deoxynucleoside triphosphates and one modified deoxynucleoside triphosphates. Extension of $S_1$ and $S_2$ forms two products, $S_1$-ext and $S_2$-ext. Extension of $B_1$ and $B_2$ results in displacement of $S_1$-ext and $S_2$-ext from the original target templates. Displaced and single-stranded $S_1$-ext serves as target for $S_2$ and $B_2$. Likewise, displaced $S_2$ ext is target for $S_1$ and $B_1$. All four primers are extended on templates $S_1$-ext and $S_2$-ext. Combined extension and displacement steps produce 2 double-stranded fragments with modified nicking enzyme recognition sites located at each end and two longer double-stranded fragments with modified recognition sites at only one end. Although the method has been described in steps, the method actually occurs simultaneously. Amplification can now proceed by the strand displacement amplification (SDA) procedure described below and described also in U.S. patent application Ser. No. 07/648,257, incorporated herein by reference.

The invention eliminates the conventional restriction step prior to binding primers. Thus workflow and costs are reduced in addition to simplifying target choice of sequences by the elimination of the need to locate target sequences flanked by convenient restriction sites. Also, the invention demonstrates increased sensitivity, provides more freedom in choosing target nucleic acid sequences for amplification, and shortens time involved in amplification.

This method for target generation can work with other amplification procedures such as polymerase chain reaction (PCR), *PCR Technology*, H. A. Erlich, Ed. (Stockton Press, New York, N.Y., 1989), transcription-based amplification system (TAS), *Proc. Natl. Acad. Sci. USA* 86:1173 (1989), ligation amplification reaction (LAR), *Genomics* 4:560 (1989), ligase based amplification system (LAS), *Gene* 89:117 (1990), and Q. B. replicase, Lomell et al., *Clin. Chem.* 35:1826 (1989), and 3SR, J. Guatelli et al., *Proc. Natl. Acad. Sci. USA* 87:1874 (1990).

If the target generation method of this invention is employed with amplification methods other than SDA, then several modifications can be made. There is no need for primers to contain any recognition sequences if subsequent amplification is by polymerase chain reaction. Likewise, if amplification is by Q beta replicase, then the recognition sequence should contain an RNA polymerase promotor for transcription of an RNA sequence recognized by Q beta replicase (F. R. Kramer et al., *Nature* 339:401 (1989). If 3SR is used to amplify the DNA then primers $S_1$ and/or $S_2$ would contain RNA polymerase promoter sites. If amplification is to proceed using a phi29 replication system (see Genentech WO 90/10064) then $S_1$ and $S_2$ would contain origin of replication sequences.

In addition, the method can be practiced by essentially repeating FIG. 1 over and over. Heat is generally applied to denature the double stranded fragments. Such a method would eliminate the need for nicking enzymes and eliminate the need for modified nucleosides. Thus the methods essentially becomes an amplification method.

Figure 2:
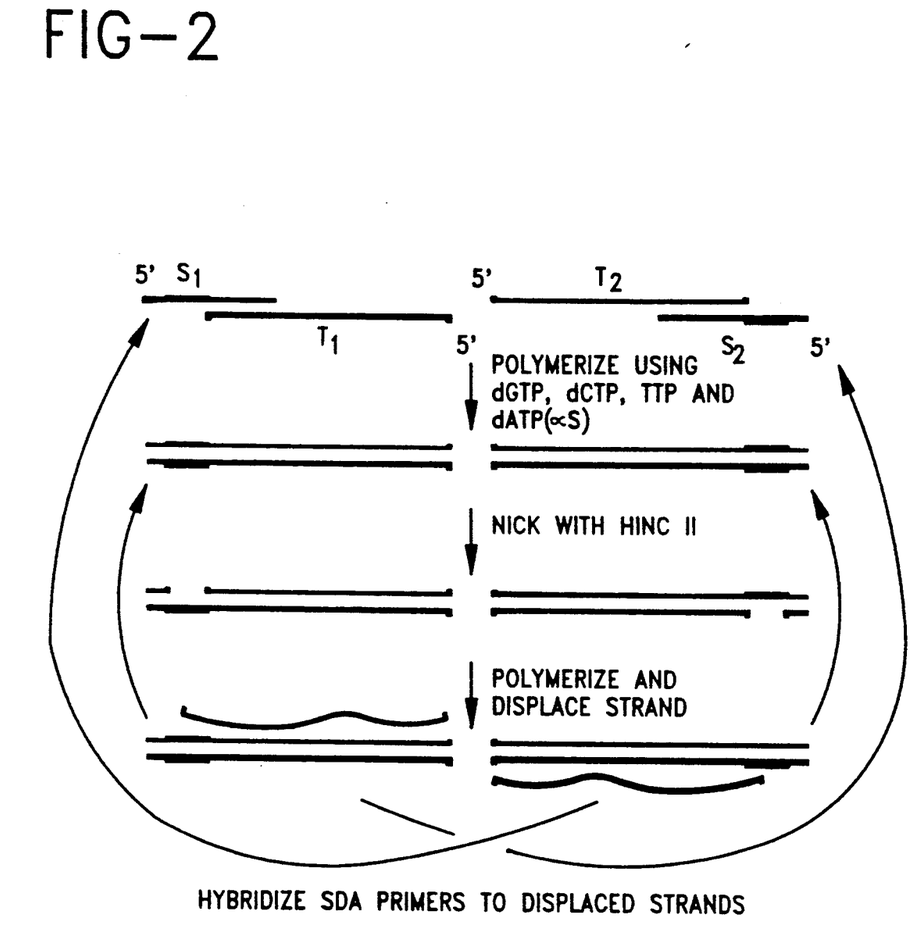

Following target generation according to the scheme in FIG. 1, the target nucleic acid sequence can now be amplified by SDA using HincII as the amplification nicking enzyme. The four target fragments at the end of FIG. 1 automatically enter a "steady state" series of amplification cycles where HincII nicks the hemiphosphorothioate recognition site, and exo$^-$ klenow extends the 3'-end at the nick while displacing the downstream strand that serves as target for the opposite SDA primer (FIG. 2). These steps continuously repeat over the course of amplification. For example, $10^7$-fold amplification theoretically derives from $\sim 23$ repetitions or cycles of the steps in FIG. 2 ($2^{23} = 10^7$). Each displaced strand in FIG. 2 contains the sequence 5'GAC at the 5'-end and the complement 5'GTC at the 3'-end. 5'GAC is the portion of the HincII recognition sequence located 3' to the nick site.

The transition between FIGS. 1 and 2 may become clearer with a detailed account for the last double stranded fragment at the bottom of FIG. 1. If HincII nicks the hemiphosphorothioate site on the left end of the fragment containing the $S_1$ primer sequence, exo$^-$–klenow initiates replication at the nick and displaces a downstream strand with 5'GAC at the 5'-end and a full complement of the primer $S_2$ at the 3'-end. $S_2$ binds this displaced strand, and exo$^-$ klenow extends $S_2$ forming the double-stranded fragment depicted as the product of the step labelled "polymerize using dGTP, dCTP, TTP and dATP ($\alpha$S)" on the right side of FIG. 2. Similar reactions occur with the entire set of fragments depicted at the bottom of FIG. 1.

The first primer (e.g., see $S_1$ and $S_2$ of FIG. 1) used in this method generally has a length of 20-100 nucleotides. Primers of approximately 25-40 nucleotides are preferred. This sequence should be substantially homologous to a sequence on the target such that under high stringency conditions binding will occur. The primer also must contain a sequence (toward the 5' end) that will be recognized by an endonucleases, if subsequent SDA occurs, and polymerases (DNA or RNA), Q beta replicases, enzymes that recognize origins of replication (such as phi29) and the like, depending on subsequent amplification procedures (referred to as "recognition sequences"). The recognition sequences generally, although not necessarily, are non palindromic when using SDA. Although two primers are preferred, only one is necessary and as many as one chooses can be employed (more amplifiable targets are generated with more primers).

The second primer (e.q., see $B_1$ and $B_2$ of FIG. 1) is designed in the manner as just described, however, the second primer does not have to contain a recognition sequence, although it may, and preferably it does contain a recognition sequence. Preferably the second set of primers are from about 8 to about 100 nucleotide bases long, more preferably the second set of primers are about 25 to about 40 nucleotide bases long, with recognition sites. If the primers do not contain recognition sites they are preferably about 10 to about 25 nucleotide bases long.

The second primer, which should bind upstream (5') of the first primer, is extended by a DNA polymerase with strand displacement ability and lacking 5'-3' exonuclease activity. As the second primer is extended, the extended product of the first primer is displaced. Although two outside or "second" primers are preferred for use, only one is necessary (e.g., $B_1$) and as many as one chooses may be employed (the more primers used in the target generation scheme (FIG. 1) the greater the number of amplifiable target fragments containing nickable recognition sites. This results in a greater amplification factor.)

If target nucleic acids are double stranded, they are denatured to render them single stranded so as to permit binding of the primers to the target strands. Raising the temperature of the reaction to approximately 95° C. is a preferred method for denaturing the nucleic acids. Other methods include raising pH; however, this will require lowering the pH in order to allow the primers to bind to the target.

If subsequent amplification of the nucleic acid targets generated is to proceed by SDA, either before or after the nucleic acids are denatured, a mixture comprising an excess of all four deoxynucleoside triphosphates wherein at least one of which is substituted (or modified), polymerase, nicking enzyme, and at least a first and second primer is also added. If high temperature is used to denature the nucleic acids, unless thermophilic enzymes are used, it is preferable to add the enzymes after denaturation. The substituted deoxynucleoside triphosphate should be modified such that it will inhibit cleavage by the nicking enzyme in the strand containing the substituted deoxynucleotides but will not inhibit cleavage on the other strand. Examples of such modified deoxynucleoside triphosphates can include 2'-deoxyadenosine 5'-O-(1-thiotriphosphate), 5-methyldeoxycytidine 5'-triphosphate, 2'-deoxyuridine 5'-triphosphate and 7deaza-2'-deoxyguanosine 5'-triphosphate.

It should be appreciated that the substitution of the deoxynucleotites may be accomplished after incorporation into a strand. For example, a methylase, such as M. Taq I, could be used to add methyl groups to the synthesized strand. And finally, if a nicking enzyme is used that only nicks one strand, the need for using modified deoxynucleotides is eliminated.

The mixture comprising the reaction components for target generation and SDA can optionally include NMP (1-methyl 2 pyrrolidinone), glycerol, poly (ethylene glycol), dimethyl sulfoxide and/or formamide. The inclusion of such organic solvents is believed to help alleviate background hybridization reactions.

It further should be appreciated that if all the nucleosides are substituted, then the polymerase need not lack the 5'→3' exonuclease activity. The presence of the substituents throughout the synthesized strand function to prevent such activity without inactivating the system.

Obviously, if SDA is not the amplification method and PCR, for example, is employed, no modified nucleotides need to be used and no nicking enzyme is required.

As described for the selection of the recognition sequence incorporated in the primer, the selection of the endonuclease used in this method should be such that it will cleave a strand at or 3' (or 5') to the recognition sequence. The endonuclease further should be selected so as not to cleave the complementary recognition sequence that will be generated in the target strand by the presence of the polymerase, and further should be selected so as to dissociate from the recognition sequence at a reasonable rate. It need not be thermophilic. Endonucleases, such as HincII, HindII, AvaI, Fnu4HI, TthlllI, and NciI are preferred.

One can envision several alternative nicking enzyme systems in addition to those detailed in this application. For example, it is generally regarded that class IIS restriction endonucleases (e.g., Fok I) contain two DNA cleavage centers within a single polypeptide unit. If one of the cleavaqe centers was inactivated, such as through site directed mutaqenesis, the resultant nicking enzyme could be used in an amplification system not requiring modified deoxynucleoside triphosphates. As an additional example, the restriction enzyme EcoRI has been shown to preferentially cleave one strand in noncanonical recognition sites or when its canonical recognition site is flanked by an oligopurine tract (Thielking et al. (1990) *Biochemistry*, 29, 4682; Lesser et al. (1990) *Science* 250, 776; Venditti & Wells (1991) *J. Biol. Chem.* 266, 16786). As another example, the restriction enzyme DpnI (available from New England Biolabs, Beverly, Mass.) cleaves a recognition site containing $me^6dA$ on both strands. DpnI or an analogous restriction enzyme may be able to nick the methyl containing strand of a hemimethylated recognition site. Such a system would employ SDA primers ($S_1$ and $S_2$) with methylated recognition sequences along with unmodified deoxynucleosidetriphosphates. Alternatively, certain restriction enzymes are known to cleave the nonmethylated strand of a hemimethylated recognition site (e.g., MspI and $me^5dC$). Such a system would use a methylated deoxynucleoside triphosphate. Finally, one could use origin of replication proteins to nick one strand of a recognition sequence.

The following chart lists enzymes, their recognition sequences and modified dNTP for use with the method:

| ENZYME | RECOGNITION SITE (5'-3') | MODIFIED dNTP |
|---|---|---|
| HincII | GTTGTAC | dATP (αS) |
| HincII | GTCAAC | dGTP (αS) |
| AvaI | CCCGAG | TTP (αS) |
| AvaI | CTCGGG | dCTP (αS) |
| NciI | CCGGG | dCTP (αS) |
| HindII | GTTGAC | dATP (αS) |
| HindII | GTCAAC | dGTP (αS) |
| Fnu4HI | GCGGC | dCTP (αS) |
| BstXI | CCAAAACCCTGG Seq ID No: 15 | TTP (αS) |
| BstXI | CCAGGTTTTGG Seq ID No: 16 | dCTP (αS) |
| BsmI | AAAGCATTC | TTP (αS) |
| BsrI | AACCAGT | TTP (αS) |
| BsaI | GGTCTCTTTTTT Seq ID No: 17 | dATP (αS) |
| NlaIV | GGAACC | TTP (αS) |
| NspI | GCATGT | dCTP (αS) |
| NspI | GCATGT | dCTP (αS) |
| NspI | GCATGT | dCTP (αS) & dGTP (αS) |
| PflMI | CCAGGTTTTGG Seq ID No: 18 | dCTP (αS) |
| HphI | GGTGAGGATCGTTT Seq ID No: 19 | dATP (αS) |
| AlwI | GGATCGTTTTT Seq ID No: 20 | dATP (αS) |
| FokI | GGATGGCATGTCTTTTGGG Seq ID No: 21 | dCTP (αS) |
| AccI | GTAGAC | dCTP (αS) |
| AccI | GTAGAC | TTP (αS) |
| AccI | GTAGAC | TTP (αS) & dCTP (αS) |
| AccI | GTCTAC | dATP (αS) |
| AccI | GTCTAC | dGTP (αS) |
| AccI | GTCTAC | dATP (αS) & dGTP (αS) |
| TthlllI | GACCACGTC | TTP (αS) |
| TthlllI | GACCACGTC | TTP (αS) & dGTP (αS) |
| TthlllI | GACGTGGTC | dCTP (αS) |
| TThlllI | GACGTGGTC | dCTP (αS) & dATP (αS) |

Polymerases, for both SDA and target generation, useful in this method include those that will initiate 5'-3' polymerization at a nick site. The polymerase should also displace the polymerized strand downstream from the nick, and, importantly, should also lack any 5'-3' exonuclease activity. Polymerases, such as the klenow fragment of DNA polymerase I and the exonuclease deficient klenow fragment of DNA polymerase I and a similar fragment from the Bst polymerase (Bio-Rad, Richmond, Calif.) are useful. SEQUENASE 1.0 and SEQUENASE 2.0 (US Biochemical), T5 DNA polymerase and Phi29 DNA polymerases also work. It should be appreciated that a polymerase ordinarily having such exonuclease activity can be deemed to "lack" such activity if that activity is blocked by the addition of a blocking agent.

An additional feature of this method is that it does not require temperature cycling. Many amplification methods require temperature cycling in order to dissociate the target from the synthesized strand. In this method, a single temperature may be employed after denaturation has occurred. The temperature of the reaction should be high enough to set a level of stringency that minimizes non-specific binding but low enough to allow specific hybridization to the target strand. In addition proper temperature should support efficient enzyme activity. From about 37° C. to about 42° C. has been found to be a preferred temperature range. Denaturation of the enzymes and nucleic acid is to be avoided.

A brief summary of the process of the invention from target generation through subsequent amplification with strand displacement amplification is a target DNA sample heat denatured in the presence of an excess of 4 primers (see FIG. 1). Two primers ($S_1$ and $S_2$) are typical SDA primers, with target binding regions at their 3'-ends and HincII recognition sequences (5'GTTGAC) at their 5'-ends. The other two primers ($B_1$ and $B_2$) consist simply of target binding regions (which can have restriction site recognition sequences but do not have to). $S_1$ and $S_2$ bind to opposite strands of the target at positions flanking the sequence to be amplified. $B_1$ and $B_2$ bind upstream of $S_1$ and $S_2$, respectively. Exo$^-$klenow simultaneously extends all 4 primers using dGTP, dCTP, TTP and dATP($\alpha$S). Extension of $S_1$ and $S_2$ forms two products, $S_1$-ext and $S_2$-ext. Extension of $B_1$ and $B_2$ results in displacement of $S_1$-ext and $S_2$-ext from the original target templates. Displaced and single stranded $S_1$-ext serves as target for $S_2$ and $B_2$. Likewise, displaced $S_2$-ext is target for $S_1$ and $B_1$. All four primers are extended on templates $S_1$-ext and $S_2$-ext. Combined extension and displacement steps produce 2 double-stranded fragments with hemiphosphorothioate HincII recognition sites at each end and two longer double stranded fragments with a hemiphosphorothioate HincII site at only one end. The four target fragments immediately enter a "steady-state" series of amplification cycles where the restriction enzyme HincII nicks the hemiphosphorothioate recognition site, and the polymerase exo$^-$ klenow initiates replication at the nick while displacing the downstream strand that serves as target for the opposite SDA primer (see FIG. 2). This amplification cycle is continuously repeated to provide excess copies of target (as previously mentioned, SDA is only one amplification method of many that can be used).

Figure 3:
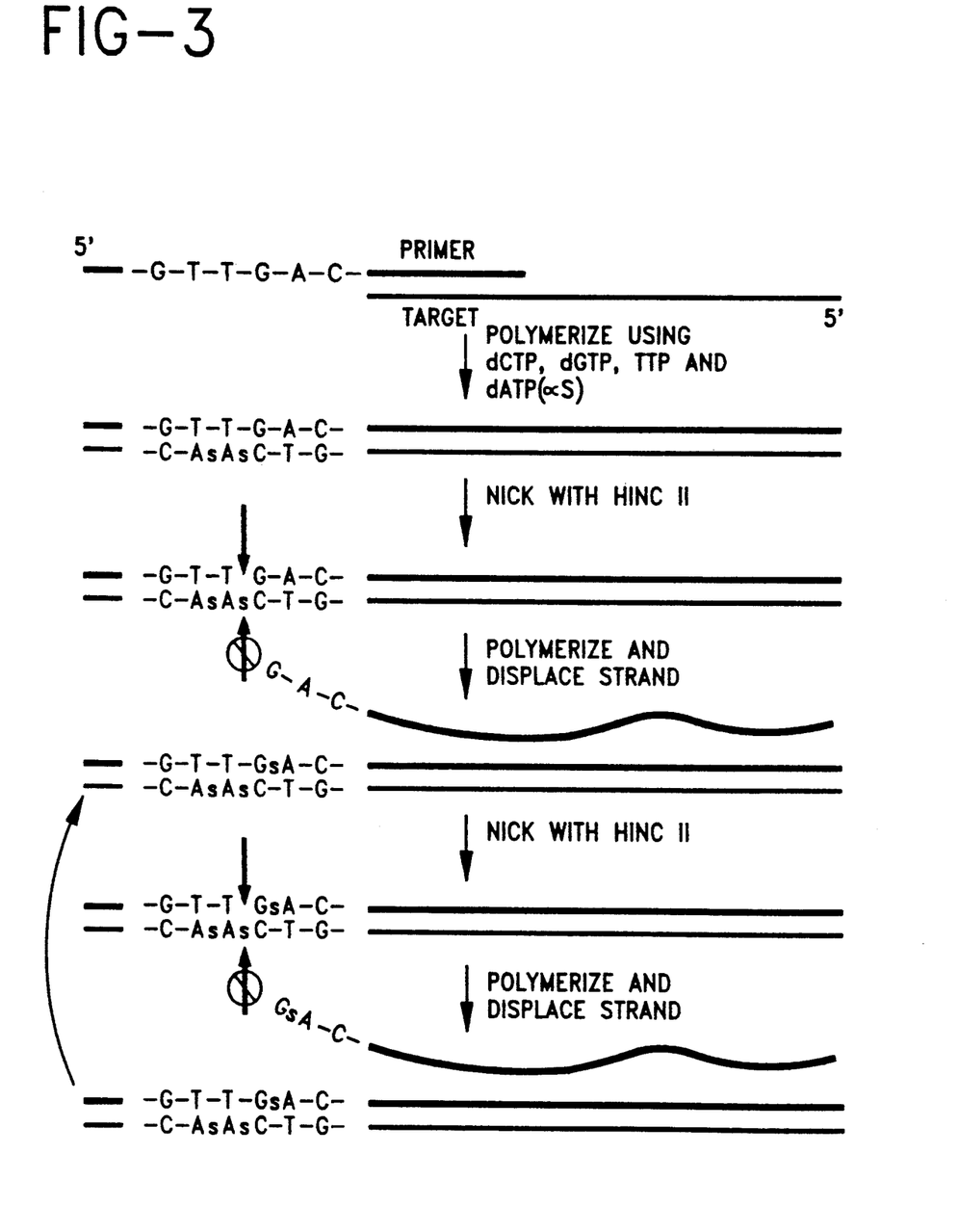
FIG. 3 Schematic showing steps of strand displacement amplification (SDA) using only one SDA primer which produces linear amplification.

Referring to FIG. 3, one example of synthesizing probes or templates for sequence an lysis using SDA is set forth. In this example, the strand labelled P represents the primer and contains at the 5' end the sequence CCGGG which is recognized by the endonuclease NciI. The strand labelled T is the target sequence which has already been fragmented and rendered single stranded. In the method, the primer binds to the target and in the presence of polymerase, deoxynucleoside triphosphates and $\alpha$thio substituted deoxycytosine triphosphate, the primer is extended the length of the target while the target is extended through the recognition sequence. In the presence of the endonuclease NciI, the primer strand is nicked between the C-G residues. In the presence of the polymerase lacking 5' to 3' exonuclease activity, the 3' end at the nick is extended, and downstream the primer strand is displaced from the target strand beginning at the nick to create a reaction product and a new strand is synthesized. In summary fashion, the newly synthesized strand will also be nicked by the endonuclease and the polymerase will then displace this strand generating another strand until either the reaction is purposefully stopped or one of the reagents becomes limiting.

An alternative to generating probes or templates for sequence analysis, as referred to in FIG. 3, is performance of exponential SDA using two primers ($S_1$ and $S_2$) wherein one primer is in excess over the other. The result is excess production of one displaced single strand over the other.

Figure 4:
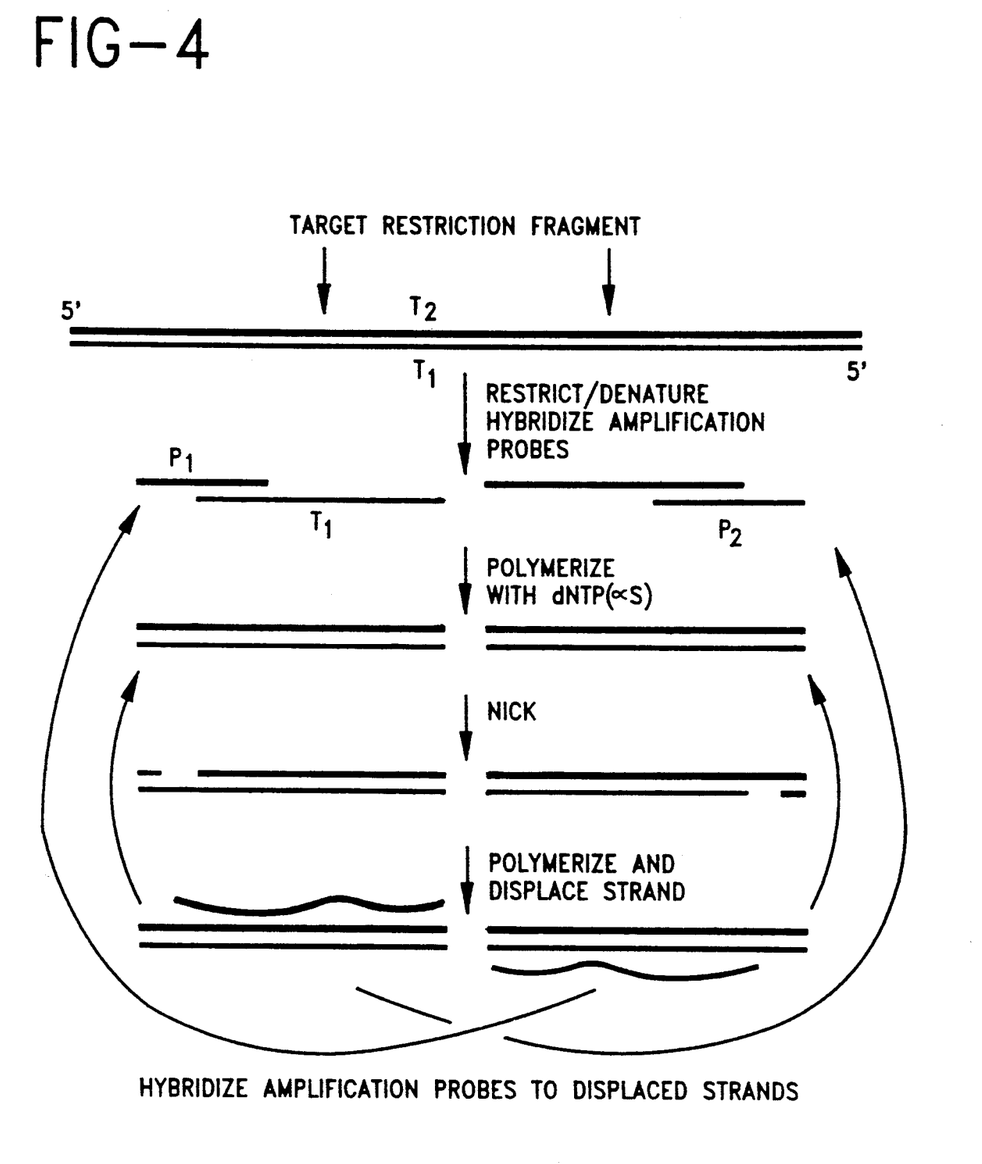
FIG. 4 Schematic showing steps of strand displacement amplification (SDA) using two SDA primers and a restriction digestion step for target generation (compared to the present invention target generation) prior to SDA. Use of two SDA primers (as opposed to one SDA primer) produces exponential amplification.

Referring to FIG. 4, an example of SDA is shown for a double stranded target fragment generated by restriction digest (in contrast the present invention target generation). There are two primers ($P_1$ and $P_2$), one each being complementary to the two target sequences ($T_1$ and $T_2$). The reaction then proceeds as described for FIG. 1. It is to be noted, however, that $P_1$ will bind to the reaction product produced from $T_2$ while $P_2$ will bind to the reaction product produced from $T_1$. In this manner, amplification proceeds logarithmically.

The presence of the amplified target can be detected by any number of methods. One method is to detect reaction products of a specific size by means of gel electrophoresis. This method is particularly useful when the nucleotides used are labelled with a radiolabel, such as $^{32}P$. Other methods include the use of labelling the nucleotides with a physical label, such as biotin. Biotin containing reaction products can then be identified by means of avidin bound to a signal generating enzyme, such as peroxidase.

Detection systems useful in the practice of this invention comprise homogeneous systems, which do not require separation, and heterogeneous systems. In each system, one or more detectable markers are used and the reaction or emission from the detection system is monitored, preferably by automated means. Examples of homogeneous systems include fluorescence polarization, enzyme mediated immunoassays, fluorescence energy transfer, hybridization protection (e.g., acridinium luminescence) and cloned enzyme donor immunoassays. Examples of heterogeneous systems include enzyme labels (such as peroxidase, alkaline phosphatase and beta-galactosidase), fluorescent labels (such as enzymatic labels and direct fluorescence labels (e.g., fluorescein and rhodamine]), chemiluminescence and bioluminescence. Liposomes or other sac like particles also can be filled with dyes and other detectable markers and used in such detection systems. In these systems, the detectable markers can be conjugated directly or indirectly to a capture moiety or the amplified products can be generated in the presence of a receptor which can be recognized by a ligand for the receptor.

One method is to detect reaction products having a specific size via electrophoresis. Another method is to radiolabel the primer sequence with $^{32}P$, for example, and then to detect the radioactivity emitted by the reaction products alone or in combination with electrophoresis. A further method is to chemically modify the primer by adding a receptor having a ligand (e.g., biotin avidin), and enzyme (e.g., alkaline phosphatase), a fluorescent dye (e.g., phycobiliprotein) or a combination thereof. Another method is to develop a detection primer which will bind to the reaction product and be extended in the presence of polymerase. The detection primer can be radiolabelled or chemically modified as described above. Many of these methods may be adapted to solid phase as well as solution phase systems. A number of these methods, as well as others, are described in U.S. Pat. Nos. 4,358,535, 4,705,886, 4,743,535, 4,777,129, 4,767,699, and 4,767,700.

The scheme in FIG. 1 can be described as two polymerase chain reaction cycles where the intervening heat denaturation step has been replaced through the use of a second pair of upstream primers ($B_1$ and $B_2$) and a DNA polymerase possessing strand displacement ability and lacking 5'-3' exonuclease activity. Consequently, the scheme may represent a general and convenient method of producing double stranded fragments with defined 5'- and 3'-ends for use in a number of applications. Applications include substituting nicking enzyme recognition sequences in $S_1$ and $S_2$ with any restriction sites in order to ligate the resultant fragments at the bottom of FIG. 1 into a cloning vector, (The scheme in FIG. 1 does not require use of a modified deoxynucleoside triphosphate), one or both of the nicking enzyme recognition sequences in the SDA primers could be substituted by RNA polymerase promoter(s) (for example bacteriophage) for production of transcription templates, and the technique could be applied to synthesis of double-stranded cDNA using a 5'→3' exonuclease deficient reverse transcriptase possessing strand displacement ability (would not require a reverse transcriptase with RNase H activity). An example of a reverse transcriptase is klenow (T. W. Myers et al., *Biochemistry* 30:7661 (1991).

The use of target preparation, as described in this invention, in conjunction with amplification procedures is not limited to any particular application. Applications for which target preparation and amplification of the invention can be used include, but are not limited to, diagnostics, amplification of RNA, (e.g., monitoring gene expression), in vitro selection and amplification of rare functional nucleic acid molecules, (see Green et al., *METHODS: A Companion to Methods in Enzymology* 2:75-86 (1991), amplification of a longer sequence followed by amplification of an internal sequence (also referred to as "nested" amplification), site directed mutagenesis, cloning, sequencing, genetic diagnosis, oncogene diagnosis, amplification of regions of unknown sequences, and non-biological applications like tracing oil spills and security identifications (see generally Erlich et al., *Science* 252:1643 (1991).

The following examples illustrate the specific embodiments of the invention described herein. As would be apparent to skilled artisans, various changes and modifications are possible and are contemplated within the scope of the invention described.

EXAMPLE 1

Target Generation

100 μL Reactions were prepared with varying amounts of target genomic DNA from *Mycobacterium tuberculosis* (M. tb). The target sequence was nucleotides 977-1023 of the IS6110 insertion element of *M. tb* (*Nucleic Acids Research* 18, 188 (1990)).

50 mM TRIS-HCl, pH 7.4
50 mM KCl
50 mM NaCl
6 mM $MgCl_2$
1 mM dGTP, dCTP, TTP, dATP(kαS)
100 μg/mL BSA
1 mM DTT
1 or 10 μg human placental DNA
3% (v/v) 1-methyl 2-pyrrolidinone
1 μM primer Seq. ID No: 10
1 μM primer Seq. ID No: 11
1 μM primer Seq. ID No: 12
1 μM primer Seq. ID No: 13
varying amounts of M. tb genomic DNA Each sample was heated 3 minutes at 98° C. followed by 2 minutes at 37° C. Then 10 units of exo$^-$ klenow (United States Biochemical) and 300 units of HincII (New England Biolabs) were added to each sample followed by incubation at 37° C. Sample aliquots (10 μL) were withdrawn after 2 hours and analyzed as follows.

Two μl of 1 μM $^{32}P$-primer Seq. ID No: 14 was added to each 10 μl sample aliquot followed by heating 2 minutes at 95° C. then 2 minutes at 37° C. Two μL of 1 unit/μL klenow (Boehringer-Mannheim, Indianapolis, Ind.) was added to samples which were then analyzed by denaturing gel electrophoresis. Strand displacement amplified products are indicated by extension of $^{32}P$-primer Seq. ID No: 14 to lengths of 35 and 56 nucleotides. Appropriate $^{32}P$ gel electrophoresis bands were excised and liquid scintillation counted. Results are summarized:

| M. tb genome copies (molecules)* | human DNA (μg)+ | electrophoresis 32p-bands (cpm)# |
|---|---|---|
| 500 | 1 | $1.9 \times 10^5$ |
| 50 | 1 | $3.9 \times 10^4$ |
| 5 | 1 | $6.1 \times 10^3$ |
| 0 | 1 | $3.3 \times 10^3$@ |
| 500 | 10 | $5.0 \times 10^4$ |
| 50 | 10 | $5.4 \times 10^3$ |
| 5 | 10 | $8.9 \times 10^2$ |
| 0 | 10 | $4.8 \times 10^2$@ |

*initial number of molecules present in the aliquot analyzed by gel electrophoresis
+amount of human placental DNA in the entire 100 μL SDA reaction
background corrected
@signal due to inadvertant contamination with trace amounts of target The amplification procedure clearly distinguishes between 5 and 0 genome copies of the target M. tb sequence. Furthermore, amplification signal is dependent on the amount of initial target, thereby providing a means for quantitative amplification and detection.

EXAMPLE 2

This example illustrates SDA using a FokI restriction step to generate target fragments prior to amplification. Two primers were synthesized on an Applied BioSystems 380B instrument using phosphoramidite chemistry and 3'-amine-ON CPG columns (Clontech Laboratories, Palo Alto, Calif.) which incorporate a primary amine at the 3' terminus. Nucleotides were ammonium deprotected and purified by denaturing gel electrophoresis. The primer sequences were:

SEQ ID NO: 1, and
SEQ ID NO: 2.

Plasmid pBR322 (Boehringer Mannheim, Indianapolis, Ind.) was serially diluted with 0.05 mg/ml *E. coli* DNA, 50 mM K acetate, 10 mM Mg acetate, 1 mM DTT, 12.5 mM TRIS (pH 7.9) at 25° C. Twenty μl samples containing 1 μg *E. coli* DNA and various amounts of pBR322 were digested 3 hours at 37° C. with 10 Units of FokI (New England Biolabs, Beverly, Mass.). The FokI digests of pBR322/*E. coli* DNA were diluted to 100 μl in the presence of 12.5 mM K acetate, 10 mM Mg acetate, 1 mM DTT, 12.5 mM TRIS (pH 7.9) at 25° C., 100 μg/ml BSA, 0.3 mM each of dATP, dGTP, TTP dCTP($\alpha$S) (Pharmacia, Piscataway, N.J.) and 0.1 μM of each primer. One set of samples underwent strand displacement amplification for 4 hours at 45° C. upon addition of 4 Units 5'→3' exonuclease deficient klenow fragment of DNA polymerase I (US Biochemical, Cleveland, Oh.) and 48 Units NciI (New England Biolabs). A second set of samples were run without the polymerase and without NciI as unamplified standards.

To detect the reaction products, a pBR322 specific detection probe, SEQ ID NO: 3, was prepared and was labelled with $^{32}$P using polynucleotide kinase. Ten μl aliquots of the amplified and unamplified Fok I/pBR322/*E. coli* DNA samples were mixed with 2 μl of 1.8 μM $^{32}$P labelled detection probe, 0.5 Units/μl Tag DNA polymerase (United States Biochemical). Samples were heated for 2 minutes at 95° C., 5 minutes at 50° C., quenched with 50% urea, and a portion was loaded onto a 10% denaturing polyacrylamide gel. The presence of amplified reaction products was detected through extension of the $^{32}$P labelled detection probe to a length of 43 or 60 nucleotides. Unamplified FokI/pBR322 was indicated by extension to 40 nucleotides. Electrophoresis $^{32}$P labelled bands were quantified by liquid scintillatoin counting subtracting appropriate background bands. The results are shown in TABLE I.

TABLE I

| # pBR322 Molecules | Amplified (±50 cpm) | Unamplified (±50 cpm) |
|---|---|---|
| 3 × 10$^8$ | 52900 | 215 |
| 3 × 10$^7$ | 18200 | 24 |
| 3 × 10$^6$ | 5690 | 21 |
| 3 × 10$^5$ | 298 | 0 |
| 0 | 37 | ND |

ND = not determined

As can be seen from TABLE I, as the amount of pBR322 DNA in the aliquot decreases, the number of counts per minute (CPM) also decreases.

EXAMPLE 3

This example illustrates SDA using a synthetic single stranded target DNA sequence. A synthetic nucleic acid target was constructed having the sequence of SEQ ID NO: 4. Primers for strand displacement amplification reaction using the restriction enzyme HincII (New England BioLabs) were synthesized to provide a 3'-NH$_2$ cap using 3'-amine-on CPG columns. The primer sequences used were:

SEQ ID NO: 5 and
SEQ ID NO: 6.

A probe for the detection of the reaction products was of the sequence: SEQ ID NO: 7. All synthetic sequences were synthesized on an Applied Biosystems 380B instrument as above, and were gel purified on 10% or 15% polyacrylamide gels containing 50% urea. Excised bands were electroeluted in ½X TBE buffer.

SEQ ID NO: 4 was diluted into 0.3 μM of the primers (i.e., SEQ ID NO: 5 and SEQ ID NO: 6) to provide a final stock concentration of 600,000 molecules of target/μl. This mixture was boiled for 3 minutes and placed at 37° C. Serial 4 fold dilutions of this stock solution were then prepared in the presence of the primers. (In the control, only amplification primers were present.)

Twenty μl of the diluted stock target solutions were added to a mixture to provide a final volume of 60 μl and a final concentration of the following components: 20 mM TRIS (pH 7.2) at 25° C., 0.1 μM of the primer sequences, 20 mM ammonium sulfate, 50 mM KCl, 50 Units HincII, 5 Units exo$^-$ klenow polymerase (US Biochemical), 1 mM DTT, 5 mM MgCl$_2$, and 300 μM each of 5'dCTP, 5'dGTP, 5'dTTP and 5'dATP($\alpha$S). The amplification reaction was allowed to proceed at 37° C. for 1 or 2 hours. In one reaction set, an additional 50 Units of HincII was added after 1 hour and the reaction was allowed to proceed for an additional hour.

At the end of the reaction times, a 10 μl aliquot of each mixture was placed on ice. To this 10 μl was added 1 μl of a 1 μM stock solution of capture probe freshly labelled with $^{32}$P. This mixture was boiled for 3 minutes and cooled to 37° C., whereupon 1 μl of 1 Unit/μl of Sequenase 2.0 (U.S. Biochemical) was added. (This enzyme will polymerize the capture probe along the full length of any reaction product when the capture probe is bound to a reaction product.) This extension reaction was allowed to proceed for 15 minutes at 37° C. To this mixture was added an equal volume of loading dyes in 50% urea. Samples were boiled again for 3 minutes before loading onto a 10% polyacrylamide gel containing 50% urea. Samples loaded on the gel represented 2.5 μl of the original 60 μl reaction mixture. Electrophoresis was allowed to proceed for 1 to 1.5 hours at 59 W after which the gel was removed and placed on film overnight at −70° C. Bands were rendered visible after exposure, were excised and quantified by liquid scintillation.

TABLE II

| # Target | 1 Hour (cpm) | 2 Hour (cpm) | 2 Hour with Additional HincII (cpm) |
|---|---|---|---|
| 0 | 0 | 0 | 0 |
| 2000 | ND | 2 | 8 |
| 8000 | 4 | 12 | 36 |
| 30,000 | 37 | 78 | 129 |
| 125,000 | 175 | 196 | 746 |
| 500,000 | 824 | 1858 | 2665 |

Referring to TABLE II, it can be seen that SDA clearly distinguishes between 0 and 30000 initial targets.

EXAMPLE 4

This is an example using a FokI restriction digest prior to SDA. The following primer sequences were used:

SEQ ID NO: 8 and
SEQ ID NO: 9.

These sequences were generated as in the other examples and were used to detect a target sequence in the plasmid pBR322.

One μg of pBR322 was digested for 2 hours at 37° C. with 8 Units of Fok I, and then was serially diluted with 0.05 mg/ml human placental DNA digested with HphI, 50 mM KCl, 5 mM MgCl$_2$, 20 mM ( 1 mM DTT and 20 mM TRIS (pH 7.2 at 25° C.). Ten μl samples containing 0.5 μg human placental DNA and various amounts of pBR322 were diluted to 100 μl in the presence of 50 mM KCl, 5 mM MgCl$_2$, 20 mM (NH$_4$)$_2$SO$_4$, 1 mM DTT and 20 mM TRIS (pH 7.2 at 25° C.) 100 μg/ml BSA, 0.1 mM each of dGTP, TTP, dCTP (Pharmacia), 0.5 mM dATP(αS) (Pharmacia) and 0.1 μM of each probe. One set of samples underwent strand displacement amplification for 3.5 hours at 39° C. upon addition of 5 Units of 5'→3' exonuclease deficient klenow fragment of DNA polymerase I and 50 Units of HincII. A second set of samples were run without polymerase and without HincII as unamplified standards.

To detect the reaction products, the pBR322 detection primer having SEQ ID NO: 7 was used having been labelled with $^{32}$P. Ten μl aliquots of the amplified and unamplified Fok I/pBR322/human placental DNA samples were mixed with 2 μl of 1 μM $^{32}$P labelled detection primer, and were heated 2 minutes at 95° C. Two Units of Sequenase 2.0 were then added, and samples were incubated for 5 minutes at 37° C. Samples were quenched with 50% urea and loaded onto a 10% denaturing polyacrylamide gel. The presence of amplified reaction products was detected through extension of the $^{32}$P labelled detection primer to lengths of 54 and 75 nucleotides. Unamplified samples were indicated by extension to 50 nucleotides. Electrophoresis of the labelled bands was quantified by liquid scintillation counting subtracting appropriated background bands. The results are shown in TABLE III.

TABLE III

| # pBR322 Molecules | Amplified (±10 cpm) | Unamplified (±10 cpm) |
| --- | --- | --- |
| $10^9$ | ND | 1963 |
| $10^8$ | ND | 257 |
| $10^7$ | ND | ND |
| $10^6$ | 135408 | ND |
| $10^5$ | 13841 | ND |
| $10^4$ | 2324 | ND |
| $10^3$ | 380 | ND |
| 0 | 139* | ND |

ND = not determined

*The amplified sample with zero added pBR322 molecules exhibited faint amplified target specific bands (54- and 75-mer) due to inadvertent contamination with pBR322.

Comparing the unamplified samples with $10^9$ and $10^8$ pBR322 molecules with respective samples containing $10^4$ and $10^3$ pBR322 molecules indicates an amplification factor of over $10^5$ fold. Further, it has been found that by adjusting the buffer comparison and deoxynucleoside triphosphate concentrations one can improve amplification performance. Inclusion of (NH$_4$)$_2$SO$_4$, a relatively low pH and a dATP(αS):dGTP ratio of 5:1 have been found to enhance amplification efficiency.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein.

---

We claim:
1. A method for generating an amplifying a nucleic acid fragment which comprises:
  (a) specifically hybridizing a first primer 5' to target nucleic acid sequence, the first primer containing a restriction enzyme recognition sequence 5' to a target binding region,

(b) simultaneously with (a), hybridizing a second primer 5' to the first primer, (c) extending the first and second primer so that the first primer extension product is displaced from the target nucleic acid sequence by extension of the second primer, (d) making the first primer extension product double stranded by synthesizing a complementary strand, and (e) amplifying the first primer extension product in an amplification reaction in which the restriction enzyme recognition site of the double stranded nucleic acid fragment is nicked by a restriction enzyme.

2. The method of claim 1 comprising hybridizing the first primer (S1) 5' to the target nucleic acid sequence, hybridizing the second primer (B1) 5' to S1, hybridizing a third primer (S2) 3' to the target sequence on the strand opposite S1 and hybridizing a fourth primer (B2) 5' to S2 such that extension of S1, S2, B1 and B2 results in displacement of the extension products of S1 and S2 by the extension products of B1 and B2.

3. The method of claim 1 in which the restriction enzyme recognition sequence is nicked by the restriction enzyme as a result of incorporation of a modified deoxynucleoside triphosphate during amplification.

4. The method of claim 3 in which the restriction enzyme recognition sequence is nicked by HincII.

5. The method of claim 3 in which the restriction enzyme recognition sequence is nicked by NciI.

6. A method for generating and amplifying a nucleic acid fragment which comprises:

(a) specifically hybridizing two single stranded primers (S1 and S2) containing HincII recognition sequences near their 5' ends to opposite nucleic acid strands flanking a double stranded target nucleic acid sequence, (b) simultaneously with (a), hybridizing two single stranded primers (B1 and B2) to opposite strands of the target nucleic acid sequence at a position 5' to the primers in (a), (c) extending all four primers in the presence of dATP ($\alpha$S) such that extension of B1 and B2 displaces a first extension product of each of S1 and S2, (d) hybridizing S1, S2, B1 and B2 to the first extension products of S1 and S2 and extending the primers in the presence of dATP ($\alpha$S) such that extension of B1 and B2 displaces a second extension product of each of S1 and S2, (e) making the second extension products double stranded by synthesizing complementary strands, and (f) amplifying the second extension products in an amplification reaction in which the double stranded HincII recognition sequence is nicked by HincII.

7. The method of claim 1 further comprising heating after step (c) and repeating steps (a)-(c).

* * * * *

UNITED STATES PATENT AND TRADEMARK OFFICE
CERTIFICATE OF CORRECTION

PATENT NO. : 5,270,184

DATED : December 14, 1993

INVENTOR(S): George T. Walker, Michael C. Little and James G. Nadeau

It is certified that error appears in the above-identified patent and that said Letters Patent is hereby corrected as shown below:

Column 23, line 67
In line 3 of Claim 1, step (a), "5'" should read --3'--.
Column 25, line 17
In line 2 of Claim 2, "5'" should read --3'--.

Signed and Sealed this

Fourth Day of June, 1996

Attest:

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

TCATTTCTTA CTTTACCGGG AAAAATCACT CAGGGTCAA     39

( 2 ) INFORMATION FOR SEQ ID NO:2:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

TCATTTCTTA CTTTACCGGG ACCCTGTGGA ACACCTACAT     40

( 2 ) INFORMATION FOR SEQ ID NO:3:

( i ) SEQUENCE CHARACTERISTICS:
    ( A ) LENGTH: 19 base pairs
    ( B ) TYPE: nucleic acid
    ( C ) STRANDEDNESS: single ( D ) TOPOLOGY: linear ( x i ) SEQUENCE DESCRIPTION: SEQ ID NO:3:

CCAGCGCTTC GTTAATACA  19

( 2 ) INFORMATION FOR SEQ ID NO:4:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

ACCCTGTGGA ACACCTACAT CTGTATTAAC GAAGCGCTGG CATTGACCCT GAGTGATTTT  60

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

GGATATTTAT TGTTGACTTA CCCTGTGGAA CAC  33

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

GGAATAATAA TATGTTGACT TGAAAAATCA CTCAG  35

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

ACATCTGTAT TAACGAAGCG  20

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

TTGAAGTAAC CGACTATTGT TGACTACCCT GTGGAACACC T  41

( 2 ) INFORMATION FOR SEQ ID NO:9:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

```
TTGAATAGTC GGTTACTTGT TGACTCAGAG AAAAATCACT CAG                                    43
```

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

```
TTGAATAGTC GGTTACTTGT TGACACTCGA CCTGAAA                                           37
```

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

```
TTGAAGTAAC CGACTATTGT TGACACTGAG ATCCCCT                                           37
```

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

```
TTGAATAGTC GGTTACTTGT TGACCCGCCA ACAAGAA                                           37
```

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

```
TTGAAGTAAC CGACTATTGT TGACCGCTGA ACCGGAT                                           37
```

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

```
CGTTATCCAC CATAC                                                                   15
```

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:15:

```
CCAAAACCCT GG                                                                      12
```

( 2 ) INFORMATION FOR SEQ ID NO:16:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

CCAGGTTTTG G                        11

( 2 ) INFORMATION FOR SEQ ID NO:17:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:17:

GGTCTCTTTT TT                      12

( 2 ) INFORMATION FOR SEQ ID NO:18:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:18:

CCAGGTTTTG G                        11

( 2 ) INFORMATION FOR SEQ ID NO:19:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:19:

GGTGAGGATC GTTT                    14

( 2 ) INFORMATION FOR SEQ ID NO:20:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:20:

GGATCGTTTT T                        11

( 2 ) INFORMATION FOR SEQ ID NO:21:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:21:

GGATGGCATG TCTTTTGGG             19